United States Patent [19]

Imbert et al.

[11] Patent Number: 4,657,911

[45] Date of Patent: Apr. 14, 1987

[54] 3-AMINO QUINUCLIDINE DERIVATIVES AND THE APPLICATION THEREOF AS ACCELERATORS OF GASTRO-INTESTINAL MOTOR FUNCTION

[75] Inventors: Thierry F. Imbert, Noisy Le Roi; Nicole A. M. Dorme, Paris; Michel Langlois, Buc, all of France

[73] Assignee: Delalande S.A., Courbevoie, France

[21] Appl. No.: 509,022

[22] Filed: Jun. 29, 1983

[30] Foreign Application Priority Data

Jul. 2, 1982 [FR] France ................. 82 11670

[51] Int. Cl.$^4$ ................ C07D 453/02; C07D 239/02; A61K 31/445; A61K 31/505
[52] U.S. Cl. .................... 514/272; 546/133; 514/305; 544/320
[58] Field of Search ............... 546/133; 544/324, 320; 514/305, 272

[56] References Cited

U.S. PATENT DOCUMENTS

| 3,534,053 | 10/1970 | Sallay et al. | 546/133 |
| 3,579,523 | 5/1971 | Sandberg et al. | 546/133 |
| 3,857,848 | 12/1974 | Mauvernay et al. | 546/133 |
| 4,093,734 | 6/1978 | Krüger et al. | 546/133 |
| 4,203,989 | 5/1980 | Yen et al. | 546/133 |

FOREIGN PATENT DOCUMENTS 2329266 11/1976 France ................ 546/133

OTHER PUBLICATIONS

Noller, Textbook of Organic Chemistry, 3rd Ed., W. B. Saunders Co., Philadelphia, 1966, pp. 166 and 226, 234.
Chem Abs., 65:2219h, Mikhlina et al.
Karrer, Organic Chemistry, Elsevier Publishing Co., Inc., New York, 1946, pp. 98, 99.
Chemical Abstracts, vol. 87, 1977, p. 513, No. 68001c.
Chemical Abstracts, vol. 65, 1966, pp. 2219-2220, No. 2220b.
Chemical Abstracts, vol. 71, 1969, p. 246, No. 38547n.
Chemical Abstracts, vol. 79, 1973, p. 311, No. 146358a.
Chemical Abstracts, vol. 86, 1977, p. 456, No. 1554189r.
Derwent Publications, Ringdoc Abstract No. 32658N.
Derwent Publications, Ringdoc Abstract No. 07429S, Abstract No. 06733V/50, USSR Pat. No. SU-414-261.
Mikhlina et al., Chemical Abstracts 76:14300d (1972).
Mikhlina et al., Derwent 163/944 (12575 M) (1972).
Bondarenko et al., Chemical Abstracts 90:72039a (1979).

Primary Examiner—Henry R. Jiles
Assistant Examiner—Robert C. Whittenbaugh
Attorney, Agent, or Firm—Lane & Aitken

[57] ABSTRACT

New derivatives of 3-amino quinuclidine of formula:

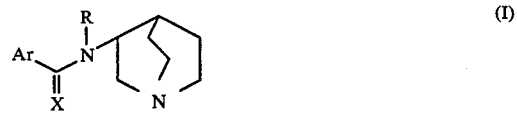

in which X=sulfur or oxygen; R=H, lower alkyl or benzyl; and Ar=substituted phenyl or substituted pyrimidinyl.

These new derivatives have utility in therapeutics as accelerators of the gastro-intestinal motor function and as medicament potentiators.

6 Claims, No Drawings

3-AMINO QUINUCLIDINE DERIVATIVES AND THE APPLICATION THEREOF AS ACCELERATORS OF GASTRO-INTESTINAL MOTOR FUNCTION

The present invention relates to new 3-amino quinuclidine derivatives, the process for preparing same and the application thereof in therapeutics.

The new derivatives of the invention correspond more precisely to the general formula:

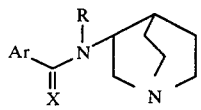 (I)

in which X represents a sulfur or oxygen atom, R designates a hydrogen atom, an alkyl group with 1 to 4 carbon atoms or the benzyl group, and Ar designates:
a phenyl nucleus substituted by a halogen atom or a lower alkyloxy group,
a phenyl nucleus of structure

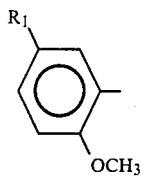

in which $R_1$ represents a halogen atom or an alkylcarbonyl group whose alkyl residue comprises 1 to 4 carbon atoms,
the (3-fluoro 2-methoxy)phenyl group,
the (2-amino 4-methoxy)5-pyrimidinyl group, or
a phenyl nucleus of structure

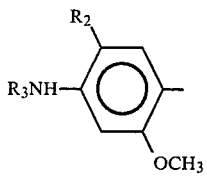

in which $R_2$ represents a halogen atom and $R_3$ represents a hydrogen atom or an alkylcarbonyl group whose alkyl residue comprises 1 to 4 carbon atoms.

Because of the presence of an asymmetric carbon in their molecule, the derivatives of formula (I) exist in the form of racemics, in the form of dextrorotatory optical isomers and in the form of levorotatory optical isomers. Therefore, the present invention includes the compounds of formula (I) under racemic form, under the form of dextrorotatory optical isomers and under the form of levorotatory optical isomers.

The present invention also relates to the acid addition salts of the derivatives of formula (I). The acids used in the preparation of these salts may be organic acids such as maleic, oxalic or fumaric acid and mineral acids such as hydrochloric acid.

The hydrates of the derivatives of formula (I) and salts thereof also come within the scope of the invention.

The N-oxides of the derivatives of formula (I) further come within the scope of the invention.

The process of the invention for obtaining the derivativee of formula (I) consists, when X represents an oxygen atom, in condensing:
either the acids of formula:

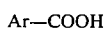 Ar—COOH (II)

in which Ar has the same meanings as in formula (I),
or the acid chlorides of formula:

 Ar—COCl (III)

in which Ar has the same meanings as in formula (I), respectively with the amino quinuclidinic derivatives of formula:

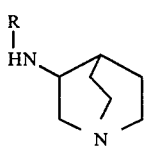 (IV)

in which R has the same meanings as in formula (I).

When the acids (II) are used, the condensation is effected by the so-called "BOISSONAS" technique, preferably in the presence of an alkyl chloroformiate and of triethylamine; when the acid chlorides (III) are used, the condensation is effected preferably in the presence of a basic agent such as triethylamine and in solution in an aprotic solvent.

Compounds (IV) are obtained by catalytic hydrogenolysis preferably by means of palladium on charcoal at 10% in an hydroalcoholic medium and in an autoclave, of the compounds of formula:

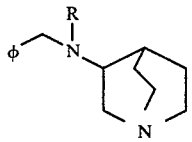 (V)

in which R has the same meanings as in formula (I).

Compounds (V) are obtained by a two stage synthesis which consists in condensing the aldehydes of formula:

 $R_5$—CHO (VI)

in which $R_5$ represents an alkyl group with 1 to 3 carbon atoms or formic aldehyde, preferably in an aqueous medium, with 3-benzylamino quinuclidine, then in reducing the intermediate compound obtained (non isolated) by means of sodium cyanoborohydride ($NaBH_3CN$).

The 3-benzylamino quinuclidine is obtained by condensing benzaldehyde with 3-amino quinuclidine (condensation effected preferably in toluene) then by reducing the Schiff base obtained by means of sodium or potassium borohydride (preferably in a methanol medium).

In the case where, in formula (I), X represents the oxygen atom and Ar represents a phenyl group having the particular structure:

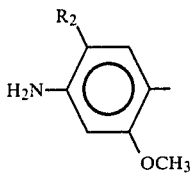

in which $R_2$ has the same meanings as before, the corresponding derivatives (I) may be obtained also by acid hydrolysis (preferably by means of 2N hydrochloric acid) of the derivatives (I) having the particular formula:

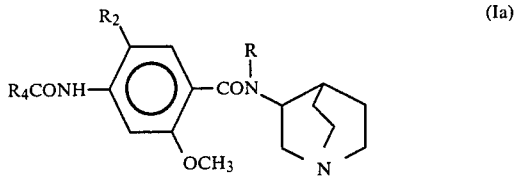

in which R and $R_2$ have the same meanings as in formula (I) and $R_4$ represents an alkyl group with 1 to 4 carbon atoms, the derivatives (Ia), being obtained in accordance with the above-stated methods.

The process of the invention for obtaining the derivatives of formula (I) for which X represents a sulfur atom consists in treating the derivatives of formula (I) for which X represents the oxygen atom:
either by the so-called "LAWESSON" reagent of formula:

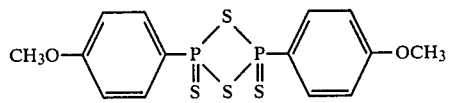

this reaction being carried out in an aprotic medium and preferably in a mixture of benzene and dioxane,
or by means of phosphorous pentasulfide, preferably in H.M.P.T.

The optical isomers according to the invention are prepared from the corresponding racemic mixtures. More precisely, they are obtained by salifying the racemic derivatives of formula (I) in base form, by means of an optically active organic acid such as L(d)-tartaric acid of D(l)-tartaric acid, then by resolving, by the method of successive fractionated recrystallizations, the salts resulting from said salification, said recrystallizations being advantageously effected in methanol.

The acid addition salts of the derivatives of formula (I) may be prepared by simple reaction of the derivatives of formula (I) with an organic or mineral acid, according to the usual methods, the derivatives of formula (I) and/or the acid being preferably used in solution in appropriate solvents.

Finally, the N-oxides of the derivatives of formula (I) are prepared according to the conventional methods described in the literature either by means of peracid (preferably M.C.P.B.A.) or hydrogen peroxide.

The following preparations are given by way of examples to illustrate the invention.

EXAMPLE 1

N-(3-quinuclidinyl)4-amino 5-chloro 2-methoxy benzamide, maleate (I)

Code number: 2

To a solution cooled to 0° C. of 12.1 g of 4-amino 5-chloro 2-methoxy benzoic acid in 300 ml of DMF are added 17.5 ml of triethylamine then 4.6 ml of ethyl chloroformiate. The solution obtained is left under agitation for 45 minutes at room temperature and to this solution is added a suspension of 12 g of 3-aminoquinuclidine dichlorhydrate and 13.2 ml of triethylamine (which has been stirred at 50° C. for an hour), at 0° C. and within 30 minutes. Then the mixture is left for 12 hours at room temperature, the DMF is evaporated, the residue is taken up in chloroform, washed with a solution of sodium carbonate, then with water, dried on sodium sulfate, filtered, the filtrate is evaporated and the residue is chromatographed on an alumina column (Eluent: chloroform-methanol 99%-1%). The compound obtained (4.3 g) is dissolved in ethyl acetate and a solution of 1.57 g of maleic acid in 30 ml of ethyl acetate is added and the precipitate obtained (3.8 g) is filtered.

Yield: 15%

Melting point: 194° C.

By the same process, but from the corresponding reagents, the compounds of formula (I) are obtained, appearing under code numbers 1, 3 to 8, 12, 15 to 18, 20, 21, 23 and 24 in the following table I.

EXAMPLE 2

N-(3-quinuclidinyl)3-fluoro benzamide, oxalate (I)

Code number: 5

A suspension of 12 g of 3-amino quinuclidine dichlorhydrate and 33.6 ml of triethylamine in 100 ml of DMF is heated at 50° C. for an hour. Then it is cooled to 0° C. and a solution of 9.5 g of 3-fluoro benzoic acid chloride in 30 ml of dimethylformamide is added within one hour. Then the mixture is left under agitation for 12 hours at room temperature, filtered, the filtrate is evaporated, the residue is taken up in methylene chloride, washed with a sodium carbonate solution, with water, dried on sodium sulfate and the solvent is evaporated. The residue is dissolved in acetone and a solution of 5.4 g of oxalic acid in acetone is added, the precipitate obtained is filtered and recrystallized in 88% ethanol. 7.4 g (yield=38%) of the expected compound are obtained.

By the same process, but from the corresponding reagents, the compounds of formula (I) are obtained shown under code numbers 1 to 4, 6 to 8, 12, 15 to 18, 20, 21, 23 and 24 in table I below.

EXAMPLE 3

Hydrated chlorhydrate of (4-amino 5-chloro 2-methoxy 1-phenyl N-(3-quinuclidinyl)-thioformamide (I)

Code number: 22

A mixture of 14.5 g of (4-amino 5-chloro 2-methoxy) 3-benzoylamino quinuclidine [(I); code number 2] and 27.1 g of LAWESSON's reagent in 500 ml of benzene and 500 ml of dioxane is heated at reflux for 3 hours. Then it is washed with concentrated NaOH, with water, the washing waters are extracted by means of ethyl acetate, the organic phases are brought together, dried on sodium sulfate and filtered and the filtrate is evaporated. The residue is chromatographed on an alumina column (eluent: ethyl acetate 90%–methanol 10%). The purified product obtained is dissolved in ethanol, hydrochloric ethanol is added to the solution obtained, the mixture is cooled and the precipitate formed is filtered and recrystallized in a methanol-water mixture (98%–2%). Thus 1.8 g of the expected product are obtained (Yield=12%).

EXAMPLE 4

Hemi-fumarate of (4-amino 5-chloro 2-methoxy)N-(3-quinuclidinyl)N-methyl benzamide (I)

Code number: 24

A solution of 45.4 g of (4-acetamido 5-chloro 2-methoxy)N-(3-quinuclidinyl)N-methyl benzamide [(I), code number 23—in base form and prepared according to anyone of the preceding examples 1 of 2] in 450 ml of 2N HCl is brought to reflux for 15 minutes. Then it is washed with ethyl acetate, basified with concentrated NaOH, extracted with chloroform, dried on sodium (or magnesium) sulfate, filtered and the filtrate is evaporated. The residue is dissolved in ethanol and an ethanol solution of fumaric acid is added and the precipitate obtained is filtered. 29.4 g (Yield=62%) of the expected product are obtained.

EXAMPLE 5

Hemi-fumarate of (4-amino 5-chloro 2-methoxy)N-(3-quinuclidinyl)N-methyl thiobenzamide (I)

Code number: 25

A solution of 12 g of sodium pentasulfide and 14.6 g of the compound (I) obtained in the preceding example (in base form) in 150 ml of H.M.P.T. is brought to 110° C. for 2 hours. Then the solution is thrown into iced water, the mixture obtained is filtered, the precipitate is taken up in basic water (aqueous NaOH) and extracted with chloroform. The chloroformic phase is dried on sodium (or magnesium) sulfate, filtered and the filtrate is evaporated; the residue is chromatographed on an alumina column (eluent: chloroform 99%–methanol 1%), then on a silica column (medium pressure liquid chromatography; eluent: chloroform 95%–methanol 4.75%–ammonia 0.25%), these chromatographies being required for eliminating the H.M.P.T. Thus 3.2 g (yield=21%) of pure product is obtained which is dissolved in ethanol, an ethanol solution of fumaric acid is added and the precipitate obtained is filtered, which corresponds to the expected product.

EXAMPLE 6

3-methylamino quinuclidine (IV)

1st step: 3-benzylamino quinuclidine

A mixture of 50 g of 3-amino quinuclidine and 40 ml of benzaldehyde in 1000 ml of toluene is brought to reflux for 45 minutes, while eliminating the water formed. Then the solvent is evaporated, the residue is dissolved in 800 ml of methanol and 15 g of potassium borohydride are added within 3 hours while maintaining the temperature at 0° C. Then the solvent is evaporated, the residue is taken up in water, the mixture obtained is extracted with ethyl acetate (or with chloroform), dried on sodium (or magnesium) sulfate, filtered and the filtrate is evaporated. Thus 85 g (yield ≃100%) of the pure expected product are obtained (one spot in TLC) which is in liquid form.

2nd step: 3-(N-methyl N-benzylamino)quinuclidine (V)

To a solution of 73.7 g of 3-benzylamino quinuclidine in water (≃300 to 400 ml) are added, while cooling to 5° C., 51 ml of a 40% aqueous formaldehyde solution. Then after the addition, the mixture is left for 30 minutes at 5° C., then 32 g of sodium cyanoborohydride are added within 1 to 2 hours. Then it is left at room temperature for 12 hours, extracted with ethyl acetate, the mixture obtained is dried on sodium (or magnesium) sulfate, filtered, the filtrate is evaporated and the residue is distilled (Boiling point [0.04 mm/Hg]=125° C.). Thus the expected product is obtained practically quantitatively.

3rd step:

A mixture of 33.3 g of 3-(N-methyl N-benzylamino)-quinuclidine and 16 g of palladium on charcoal at 10% (50% humidity) in 500 ml of ethanol is heated in an autoclave at 80° C. for 6 hours 30 minutes and under a hydrogen pressure of 6 bars. Then it is filtered, the solvent is evaporated (under a good vacuum and when cold) and the residue is distilled (Boiling point [24 mm/Hg]=110° C.). Thus the expected product is obtained with a yield of 43%.

EXAMPLE 7 chlorhydrate of dextrorotatory (26) and levorotatory (27) meta-chloro (3-N-quinuclidinyl)benzamides To 52.5 g of racemic meta-chloro (3-N-quinuclidinyl)benzamide [(I), code number 20], in base form, is added a solution of 29.7 g of dextrorotatory L tartaric acid in 500 ml of methanol, the mixture obtained is brought to reflux, filtered when hot and left to cool. 47 g of precipitate (melting point ≃178° C.) are obtained after filtration, which are redissolved in 500 ml of boiling methanol. After cooling and filtration, 28 g of precipitate (melting point ≃188° C.) are obtained, which are dissolved in 250 ml of boiling methanol. After cooling and filtration, 20 g of compound (melting point ≃192° C.) are obtained which are dissolved in water, the aqueous solution obtained is basified by means of sodium carbonate, extracted with chloroform, dried on sodium sulfate, filtered and the filtrate is evaporated. The product obtained is dissolved in acetone and hydrochloric ethanol (≃6N) is added, the precipitate obtained is filtered and recrystallized in ethanol. Thus, 9.4 g of dextrorotatory isomer (27) are obtained: $\alpha_D^{20}$ (methanol), $C≃2.5$)=+15.1°, melting point=240° C. [the corresponding base has a $\alpha_D^{20}$ (methanol, $C≃2.5$)=+33.3° and a melting point=125° C.]. The mother waters (filtrates) of the first three recrystallizations in methanol are brought together, evaporated, the residue is taken in water, the mixture obtained is basified by means of sodium carbonate, extracted with chloroform, the extract is dried on sodium (or magnesium) sulfate, filtered and the filtrate is evaporated. 42 g of product are obtained to which is added a solution of 23.8 g of levorotatory D tartaric acid in 500 ml of methanol; the mixture is brought to reflux, filtered when hot, then after cooling of the filtrate, the precipitate obtained is filtered (melting point=186° C.). This precipitate is dissolved in 350 ml of boiling methanol, the solution is filtered when hot, then after cooling of the filtrate, the precipitate obtained is filtered. Thus 25 g of a precipitate are obtained (melting point=192° C.) which is dissolved in water. The solution is basified by means of sodium carbonate, extracted with chloroform, the extract is dried on sodium (or magnesium) sulfate, filtered and the filtrate evaporated, the residue is dissolved in acetone and hydrochloric ethanol ($\simeq$6N) is added. The precipitate obtained is filtered and recrystallized in ethanol ($\simeq$100 ml). Thus 10.9 g of levorotatory isomer (27) are obtained: $\alpha_D^{20}$ (methanol, C$\simeq$2.5)=$-$15.4°, melting point=240° C. [the corresponding base has a $\alpha_D^{20}$ (methanol, C$\simeq$2.5)=$-$34.3° and melting point=125° C.].

TABLE I (I)

$$Ar-\underset{\underset{X}{\|}}{C}-\underset{R}{N}H-\text{(quinuclidinyl)}$$

| Code number | Ar–C(=X)– | R | Form | Empirical formula | Molecular weight | Melting point (°C.) | ELEMENTARY ANALYSIS % | C | H | N |
|---|---|---|---|---|---|---|---|---|---|---|
| 1 | 2-amino-5-(methoxymethylene)pyrimidine-CO– (H$_2$N–pyrimidine with =CH–CO– and OCH$_3$) | H | Hydrated Base | C$_{13}$H$_{19}$N$_5$O$_2$ +0.5% H$_2$O | 277.32 | 198 | Cal. Obt. | 55.97 55.61 | 6.82 6.70 | 25.12 25.43 |
| 2 | 4-amino-2-chloro-5-methoxyphenyl–CO– | " | Maleate | C$_{19}$H$_{24}$ClN$_3$O$_6$ | 425.86 | 194 | Cal. Obt. | 53.58 53.32 | 5.68 5.78 | 9.87 9.97 |
| 3 | 3-methoxyphenyl–CO– | " | Oxalate | C$_{17}$H$_{22}$N$_2$O$_6$ | 350.36 | 188 | Cal. Obt. | 58.27 58.15 | 6.33 6.47 | 8.00 7.89 |
| 4 | 4-fluorophenyl–CO– | " | " | C$_{16}$H$_{19}$FN$_2$O$_5$ | 338.33 | 232 | Cal. Obt. | 56.80 56.52 | 5.66 5.66 | 8.28 8.27 |
| 5 | 3-fluorophenyl–CO– | " | " | C$_{16}$H$_{19}$FN$_2$O$_5$ | 338.33 | 223 | Cal. Obt. | 56.80 56.73 | 5.66 5.72 | 8.28 8.27 |
| 6 | 2-fluorophenyl–CO– | " | HCl | C$_{14}$H$_{18}$FClN$_2$O | 284.76 | 238 | Cal. Obt. | 59.05 58.97 | 6.37 6.35 | 9.84 9.84 |
| 7 | 2-methoxyphenyl–CO– | " | Oxalate | C$_{17}$H$_{22}$N$_2$O$_6$ | 350.36 | 188 | Cal. Obt. | 58.27 58.29 | 6.33 6.55 | 8.00 8.12 |
| 8 | 4-methoxyphenyl–CO– | " | Hydrated HCl | C$_{15}$H$_{21}$ClN$_2$O$_2$ +H$_2$O | 314.84 | 190 | Cal. Obt. | 57.23 57.47 | 7.36 6.92 | 8.90 8.83 |

TABLE I-continued (I)

Ar—C(=X)—N(R)—[3-quinuclidinyl]

| Code number | Ar—C(=X)— | R | Form | Empirical formula | Molecular weight | Melting point (°C.) | ELEMENTARY ANALYSIS % | C | H | N |
|---|---|---|---|---|---|---|---|---|---|---|
| 12 | 5-Br, 4-H$_2$N, 2-OCH$_3$ benzoyl | " | HCl | C$_{15}$H$_{21}$BrClN$_3$O$_2$ | 389.70 | >260 | Cal. Obt. | 46.11 45.69 | 5.42 5.35 | 10.76 10.51 |
| 15 | 5-Cl, 2-OCH$_3$ benzoyl | " | " | C$_{15}$H$_{20}$Cl$_2$N$_2$O$_2$ | 331.24 | 215 | Cal. Obt. | 54.39 54.07 | 6.09 6.25 | 8.46 8.33 |
| 16 | 5-CH$_3$CO, 2-OCH$_3$ benzoyl | " | " | C$_{17}$H$_{23}$ClN$_2$O$_3$ | 338.83 | 245 | Cal. Obt. | 60.26 60.03 | 6.84 6.91 | 8.27 8.20 |
| 17 | 5-F, 2-OCH$_3$ benzoyl | " | " | C$_{15}$H$_{20}$ClFN$_2$O$_2$ | 314.78 | 246 | Cal. Obt. | 57.23 57.36 | 6.40 6.31 | 8.90 8.92 |
| 18 | 5-Br, 2-OCH$_3$ benzoyl | " | " | C$_{15}$H$_{20}$ClBrN$_2$O$_2$ | 375.69 | 220 | Cal. Obt. | 47.95 47.80 | 5.37 5.58 | 7.46 7.48 |
| 20 | 3-Cl benzoyl | " | " | C$_{14}$H$_{18}$Cl$_2$N$_2$O | 301.21 | 242 | Cal. Obt. | 55.82 55.53 | 6.02 6.08 | 9.30 9.35 |
| 21 | 3-F, 2-OCH$_3$ benzoyl | " | Base | C$_{15}$H$_{19}$FN$_2$O$_2$ | 278.32 | 125 | Cal. Obt. | 64.73 64.47 | 6.88 7.00 | 10.07 10.00 |
| 22 | 2-Cl, 4-H$_2$N, 5-OCH$_3$ thiobenzoyl | " | 1.05 HCl +0.5% H$_2$O | C$_{15}$H$_{21}$Cl$_2$N$_3$OS +0.5% H$_2$O +0.05 HCl | 365.97 | >260 | Cal. Obt. | 49.22 48.26 | 5.86 5.54 | 11.48 11.51 |

TABLE I-continued $$Ar-\underset{X}{\overset{R}{\underset{\|}{C}}}-N\underset{N}{\overset{}{\bigcirc}} \quad (I)$$

| Code number | Ar—C— ‖ X | R | Form | Empirical formula | Molecular weight | Melting point (°C.) | ELEMENTARY ANALYSIS % C H N | | | |
|---|---|---|---|---|---|---|---|---|---|---|
| 23 | Cl / CH₃CONH—⟨⟩—CO— \ OCH₃ | CH₃ | Maleate | $C_{22}H_{28}ClN_3O_7$ | 481.92 | 237 | Cal. 54.82 5.85 8.72<br>Obt. 54.96 6.07 8.43 | | | |
| 24 | Cl / H₂N—⟨⟩—CO— \ OCH₃ | " | ½ fumarate +1.35% H₂O | $C_{18}H_{24}ClN_3O_4$ +1.35% H₂O | 387.08 | >260 | Cal. 55.85 6.40 10.86<br>Obt. 55.79 6.29 10.50 | | | |
| 25 | Cl / H₂N—⟨⟩—CS— \ OCH₃ | " | ½ fumarate +11.7% H₂O | $C_{18}H_{24}ClN_3O_3S$ +11.7% H₂O | 444.32 | 194 | Cal. 48.00 6.67 9.33<br>Obt. 47.83 6.00 9.35 | | | |
| 26 | Cl—⟨⟩—CO— | H | HCl dextrorotatory | $C_{14}H_{18}Cl_2N_2O$ | 301.21 | 240 | Cal. 55.82 6.02 9.30<br>Obt. 55.70 6.18 9.39 | | | |
|  |  |  | Base dextrorotatory | $C_{14}H_{17}ClN_2O$ | 264.75 | 125 | Cal. — — —<br>Obt. — — — | | | |
| 27 | Cl—⟨⟩—CO— | H | HCl levorotatory | $C_{14}H_{18}Cl_2N_2O$ | 301.21 | 240 | Cal. 55.82 6.02 9.30<br>Obt. 55.71 6.20 9.27 | | | |
|  |  |  | Base levorotatory | $C_{14}H_{17}ClN_2O$ | 264.75 | 125 | — — — — | | | |
|  |  |  |  |  |  |  | Cal.<br>Obt. | | | |

The compounds of the invention have been tested on laboratory animals and showed activity on the digestive system (particularly as accelerators of the gastro-intestinal motor function). This activity was shown:

by the gastric evacuation test on rats, carried out with the following method: The compounds of the invention are administered orally together with 20 steel balls to wakeful rats having eaten nothing for 20 hours. The action on the gastric evacuation of the tested compounds was evaluated 90 minutes after administration thereof by the percentage of animals whose stomach contained no balls, these balls being counted by radiological examination. To illustrate the invention, some results obtained with the compounds of the invention are given in table II below;

by the total transit test in rats, carried out according to the following method: The compounds of the invention were administered orally simultaneously with 20 steel balls to wakeful rats having eaten nothing for 20 hours. The fast was broken immediately after the administration and the compounds of the invention were administered a second time at the same dose after a period of 7 hours. The total transit was evaluated 24 hours after the first administration of the compounds to be tested by the percentage of the animals having evacuated all the balls in the faeces, the balls being counted by radiological examination. To illustrate the invention, some results obtained with the compounds of the invention are shown in table III below.

In addition, the acute toxicity in mice was evaluated according to the method of MILLER and TAINTER described in Proc. Soc. Exp. Biol. Med. 57 261 (1944).

TABLE II

| Code number of the compounds tested | $LD_{50}$ toxicity - mice (mg/kg/i.p.) | Dose administered (mg/kg/p.o.) | % animals whose stomach contained no ball after 90 minutes |
|---|---|---|---|
| 2 | 105 | 5 | 75 |
|  |  | 10 | 100 |
| 3 | 110 | 2.5 | 100 |

TABLE II-continued

| Code number of the compounds tested | LD$_{50}$ toxicity - mice (mg/kg/i.p.) | Dose administered (mg/kg/p.o.) | % animals whose stomach contained no ball after 90 minutes |
|---|---|---|---|
| 5 | 140 | 2.5 | 100 |

TABLE III

| Code number of the compounds tested | LD$_{50}$ toxicity - mice (mg/kg/i.p.) | Dose administered (mg/kg/p.o.) | % animals having completely evacuated the balls after 24 hours |
|---|---|---|---|
| 2 | 105 | 1 | 64 |
| 7 | 150 | 10 | 50 |
| 6 | 150 | 10 | 55 |
| 17 | 140 | 1 | 57 |
| 18 | 160 | 1 | 38 |
| 22 | 300 | 1 | 63 |
| 1 | 300 | 10 | 50 |
| 20 | 145 | 1 | 50 |
| 23 | 50 | 1 | 38 |
| 24 | 70 | 1 | 38 |
| 25 | 80 | 1 | 44 |

As the above tables show, the difference between the toxic doses and the active doses allows use to be made in therapeutics of the compounds of the invention in the field of the digestive system and more particularly as accelerator of the gastro-intestinal motor function and as a medicament potentiator, particularly of analgesic medicaments such as aspirin or paracetamol for example.

The present invention also relates therefore, as medicaments, and more especially as medicaments useful in the field of the digestive system, to the derivatives of formula (I), the pharmaceutically acceptable acid addition salts thereof, the hydrates of these derivatives and salts and the N-oxides of these derivatives.

The invention extends finally to the pharmaceutic compositions containing, as active ingredient, at least one of the above-defined medicaments, in association with an appropriate vehicle. These compositions may be administered orally, in the form of capsules, tablets, pills etc. . . at doses which may reach 500 mg of active ingredient per day (taken in one or several doses per day) or parenterally in the form of an injectable solute at doses which may reach 200 mg of active principle per day (in 1 or 2 daily injections).

We claim:

1. 3-amino quinuclidine derivatives corresponding to the formula:

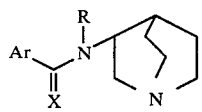
(I)

in which X represents a sulfur or oxygen atom, R designates a hydrogen atom, an alkyl group with 1 to 4 carbon atoms or the benzyl group, and Ar designates:
- a phenyl nucleus substituted by a halogen atom or a lower alkyloxy group,
- a phenyl nucleus of structure

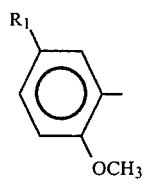

in which $R_1$ represents a halogen atom or an alkylcarbonyl group whose alkyl residue comprises 1 to 4 carbon atoms,
the (3-fluoro 2-methoxy)phenyl group,
the (2-amino 4-methoxy)5-pyrimidinyl group, or
a phenyl nucleus of structure

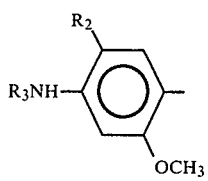

in which $R_2$ represents a halogen atom and $R_3$ represents a hydrogen atom or an alkylcarbonyl group whose alkyl residue comprises 1 to 4 carbon atoms,
as well as the dextrorotatory or levorotatory optical isomers corresponding to these derivatives, the organic or mineral acid addition salts of these derivatives and optical isomers, the hydrates of these derivatives, optical isomers and salts and the N-oxides corresponding to these derivatives and optical isomers.

2. The compounds as claimed in claim 1, for which the pair (X, R) takes the value (O, H) and Ar takes any one of the following values:

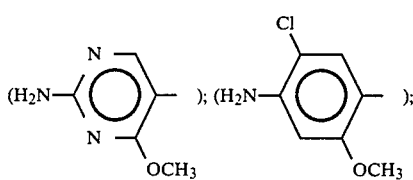

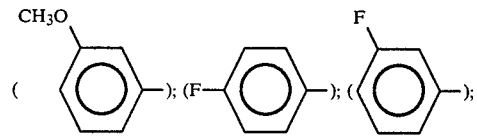

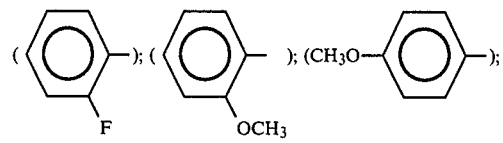

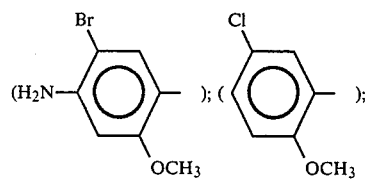

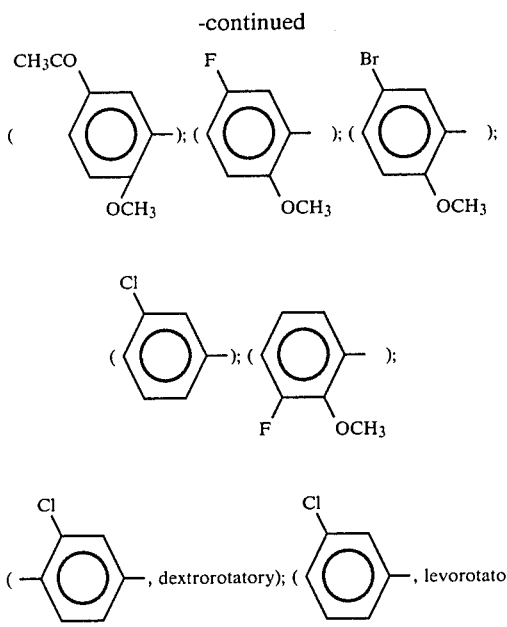

3. The compounds as claimed in claim 1, for which the pair (X, R) takes the value (O, CH₃) and Ar takes any one of the following values:

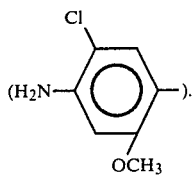

4. The compounds as claimed in claim 1, for which the pair (X, R) takes the value (S, H) or (S, CH₃) and Ar takes the value 5. A pharmaceutical composition useful as an accelerator of the gastro-intestinal motor function comprising (a) a therapeutically effective amount of at least one compound according to claim 1 and (b) a pharmaceutically acceptable carrier.

6. A method of use of a therapeutically effective amount of a compound of any one of claims 1, 2, 3 or 4 as an accelerator of the gastro-intestinal motor function.

* * * * *